United States Patent [19]

Razdan et al.

[11] 4,423,221
[45] Dec. 27, 1983

[54] 7-CARBOETHOXY-MORPHINAN-6-ONE COMPOUNDS

[75] Inventors: Raj K. Razdan, Belmont; Haldean C. Dalzell, Weston, both of Mass.

[73] Assignee: S/SA Pharmaceutical Laboratories, Inc., Cambridge, Mass.

[21] Appl. No.: 386,921

[22] Filed: Jun. 10, 1982

[51] Int. Cl.³ ............... C07D 221/28; A61K 31/485
[52] U.S. Cl. ............................. 546/74; 424/260
[58] Field of Search ..................... 546/44, 45, 46, 74

[56] References Cited

U.S. PATENT DOCUMENTS 2,178,010 10/1939 Small et al. .
4,347,361 8/1982 Quick et al. ........................ 546/45
4,374,139 2/1983 Mohacsi ............................. 424/260

OTHER PUBLICATIONS

Quick et al., J. Med. Chem., vol. 25, No. 8, pp. 983–986 (8/82).
Herlihy et al., J. Med. Chem., vol. 25, No. 8, pp. 986–990 (8/82).
Kotick et al., J. Med. Chem., vol. 23, No. 2, pp. 166–174 (2/80).
Bentley & Hardy, *Journal of the American Chemical Society*, 89:13, pp. 3267–3273.
Rearick & Gates, *Tetrahedron Letters*, 507 (1970).
Sawa et al., *Tetrahedron*, 15, 144 (1961).
Leland et al., *J. Med. Chem.*, 23, 1427 (1980).

*Primary Examiner*—Diana G. Rivers
*Attorney, Agent, or Firm*—Jerome L. Jeffers

[57] ABSTRACT

The present invention involves 7-carboethoxymorphinan-6-one compounds of the formula:

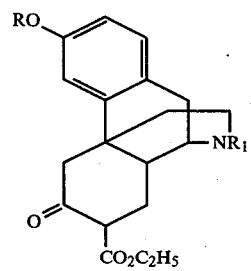

These compounds are useful as analgesic and/or narcotic antagonists.

11 Claims, No Drawings

7-CARBOETHOXY-MORPHINAN-6-ONE COMPOUNDS

BACKGROUND OF THE INVENTION

Certain well-known narcotic analgesics belong to the class of 4,5α-epoxymorphinan compounds which have the following basic ring system in which the atoms are numbered as indicated:

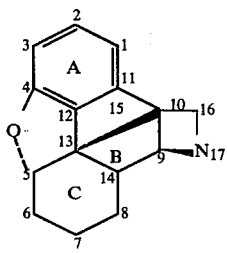

(I)

The two most familiar compounds of this class are morphine and its 3-methyl ether, codeine, with the structures indicated below:

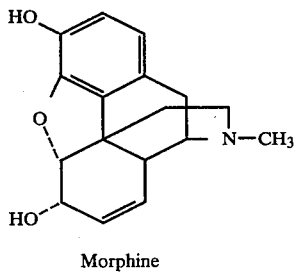

Morphine (II)

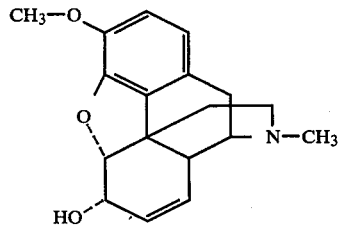

Codeine

When the 6-hydroxyl group of each of these compounds is oxidized to an oxo group, the compounds conveniently are referred to as morphinone and codeinone, respectively. When the N-methyl groups of the latter compounds are replaced by other substituent groups they may be referred to as N-substituted normorphinones and norcodeinones, respectively. There are two types of nomenclature commonly used for describing compounds herein. The trivial names, such s morphine or morphinone, are widely accepted and used for the sake of brevity and clarity. The Chemical Abstracts nomenclature is preferred and is used wherever precision is needed.

The numbering and stereochemical placement of atoms in the morphinan system is depicted in formula I. A dashed line is used to represent a covalent bond projecting below the plane of a reference atom (α-configuration) while a wedged or heavily accented line signifies a covalent bond above such plane (β-configuration). The serpentine line at the 14-position of formula I is intended to denote the orientation of the covalent bond as being either above or below the plane of reference. The compounds of this invention have the same stereochemical placement of atoms as indicated in the formula I unless otherwise indicated. Another feature of the stereochemistry of the morphinan nucleus is that when the hydrogen in the 14-position is in the β-configuration, the compounds have the same B/C ring junction as the naturally occurring morphine alkaloids and are referred to as B/C cis isomers. Conversely, when the 14-hydrogen atom is in the α-configuration the compounds are in the B/C trans-configuration and are referred to as isomorphinans.

Morphine and its relatives are used primarily for the relief of pain (i.e., as analgesics). They are narcotic and possess dependence-inducing ability and produce other side effects that make them less than ideal analgesics (emesis, constipation, sweating, respiratory depressions, miosis). A compound with the appropriate profile of analgesic (agonist) and narcotic antagonist actions which is not morphine-like has potential as an analgesic agent for treatment of moderate to severe pain without liability of drug dependence.

Furthermore, a compound having only strong narcotic antagonist action may be a desirable agent for treatment of drug dependence.

Bentley and Hardy disclose in *Journal of the American Chemical Society*, 89:13, Pp. 3267-73, certain Diels-Alder adducts of thebaine having the formula:

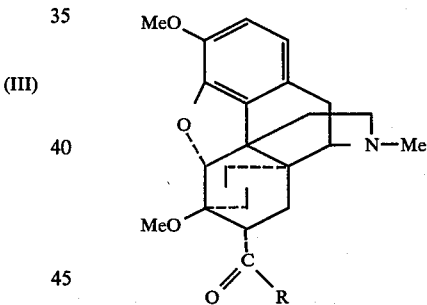

(III)

where R is methyl or phenyl. It is stated that these compounds possess analgesic activity.

Co-pending application U.S. Ser. No. 215,051 (filed Dec. 10, 1980), now U.S. Pat. No. 4,347,361, discloses 4,5α-epoxy-3-hydroxy or methoxy-7-(1-hydroxyalkyl or 1-oxoalkyl) morphinan-6-one compounds characterized by the structural formulae:

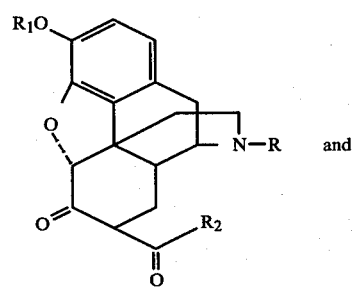

and

-continued

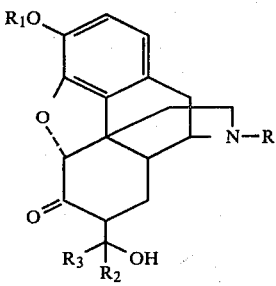

In the foregoing formulae, R is methyl, propargyl, cyclopropylmethyl, etc. Small et al disclose in U.S. Pat. No. 2,178,010 (issued Oct. 31, 1939) the reaction of dihydrothebaine:

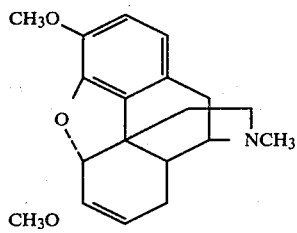

with methylmagnesium iodide in refluxing ether solution for 108 hours to give, after workup which includes acid hydrolysis, a mixture from which may be isolated in 45–58% crude yield (15–17.5% rerystallized) methyl dihydrothebainone:

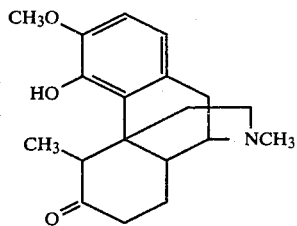

and a 9–11% yield (5–6% recrystallized) of isomethyl-dihydrothebainone:

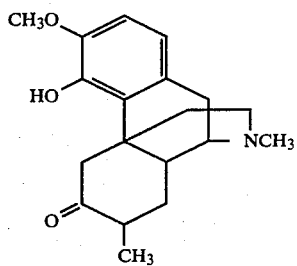

The introduction of a 7-ketone into the morphinan nucleus with concurrent cleavage of the 4,5 epoxy bond has been reported by Rearick and Gates in Tetrahedron Letters, 507 (1970). They report that treatment of 14-bromocodeinone:

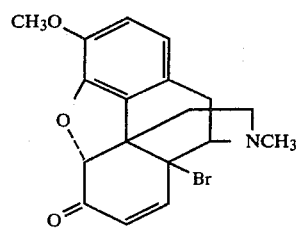

with Claisens alkali gives the 7-Keto morphinane.

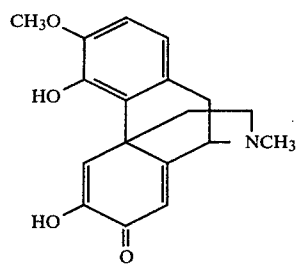

Sawa et al report the preparation of desoxysinomenine characterized by the formula:

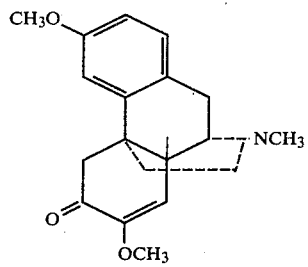

and desoxydihydrosinomenine characterized by the formula:

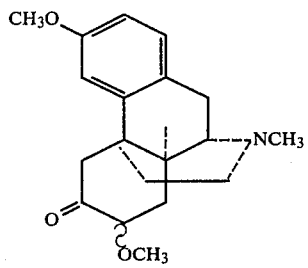

in Tetrahedron, 15, 144 (1961) from the naturally occurring alkaloid, sinomenine:

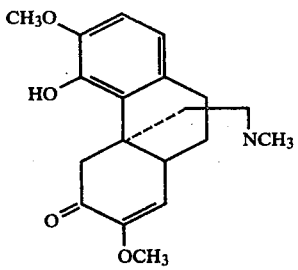

SUMMARY OF THE INVENTION

The present invention involves 7-carboethoxymorphinan-6-one compounds characterized by the formula:

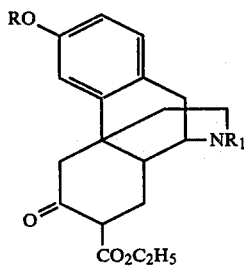

In the above formula, R is H or methyl and $R_1$ is methyl, cyclobutylmethyl, cyclopropylmethyl, propargyl, allyl, dimethylallyl or furfuryl.

DESCRIPTION OF THE INVENTION

The preparation of the compounds of the present invention where $R_1$ is methyl or cyclopropyl methyl is illustrated by scheme I. Referring to scheme I, catalytic reduction (Pd/c) of 4-desoxydihydrothebaine-φ (1) (Sawa et al, Tetrahedron, 15, 154 [1961]) in acetic acid containing trifluoroacetic acid gave a mixture of 3-methoxy-17-methylmorphinan-6-one (2a) and 3-methoxy-17-methyl-14α-morphinan-6-one (2b). Separation by chromatography afforded 54% (2a (Sawa et al, Tetrahedron, 20, 2247 [1964]) and 33% 2b (Sawa et al, Tetrahedron, 21, 1133 [1965]). Reaction of 2a or 2b with sodium hydride and diethylcarbonate in refluxing benzene formed the 7-carboethoxy derivatives (3a) and (3b), which on treatment with borontribromide in chloroform furnished the 3-hydroxy compounds, (4a) and (4b).

Compounds 2a and 2b were converted to the corresponding N-(cyclopropylmethyl) compounds (5a) and (5b), respectively. Treatment of 2a or 2b with potassium carbonate and cyanogen bromide followed by acid hydrolysis gave the corresponding nor compounds which were treated with cyclopropylmethylbromide to give compounds 5a and 5b as previously reported by Polazzi et al in J. Med. Chem., 23, 174 (1980). Compounds 5a and 5b were then converted to 6a and 6b and demethylated to 7a and 7b, respectively, in the manner described above. Those compounds in which $R_1$ is cyclobutylmethyl, propargyl, allyl, dimethylallyl or furfuryl can be prepared in a manner analagous to the conversion of (2) to (5) in scheme I using the appropriate reactants, i.e., cyclobutylmethylbromide, propargyl bromide, allyl bromide, dimethylallyl bromide and furfuryl bromide, respectively. Alternatively, the preparation of the 3-hydroxy-17-substituted compounds can be accomplished by first adding the substituent to the 17-position and then converting the 3-methoxy to a 3-hydroxy group. The preparation of these compounds is further illustrated by the following examples. In these examples, melting points were determined on a Thomas-Hoover melting point apparatus and are uncorrected. The NMR spectra were recorded on a Varian T-60 spectrometer using tetramethylsilane as an internal standard. Infrared spectra were obtained on a Perkin-Elmer 700 spectrometer and HPLC analyses were performed on a Waters Associates A 202 chromatograph. Microanalyses were performed by Atlantic Microlab, Inc., Atlanta, Ga., and mass spectra were obtained from the Mass Spectrometary Facility, Cornell University, Ithaca, N.Y. Except as noted, all reagents and solvents were used as obtained from the supplier. Tetrahydrofuran was distilled from sodium ketal and benzene was passed through a neutral alumina column and stored over molecular sieves.

SCHEME I

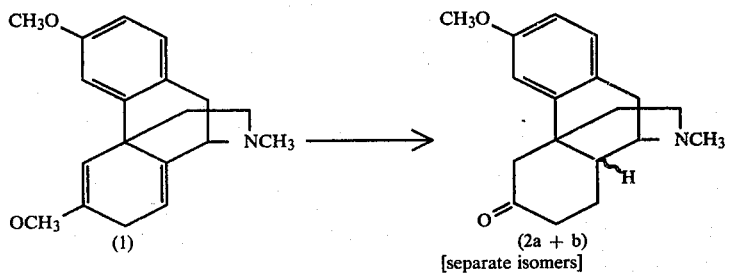

SCHEME I

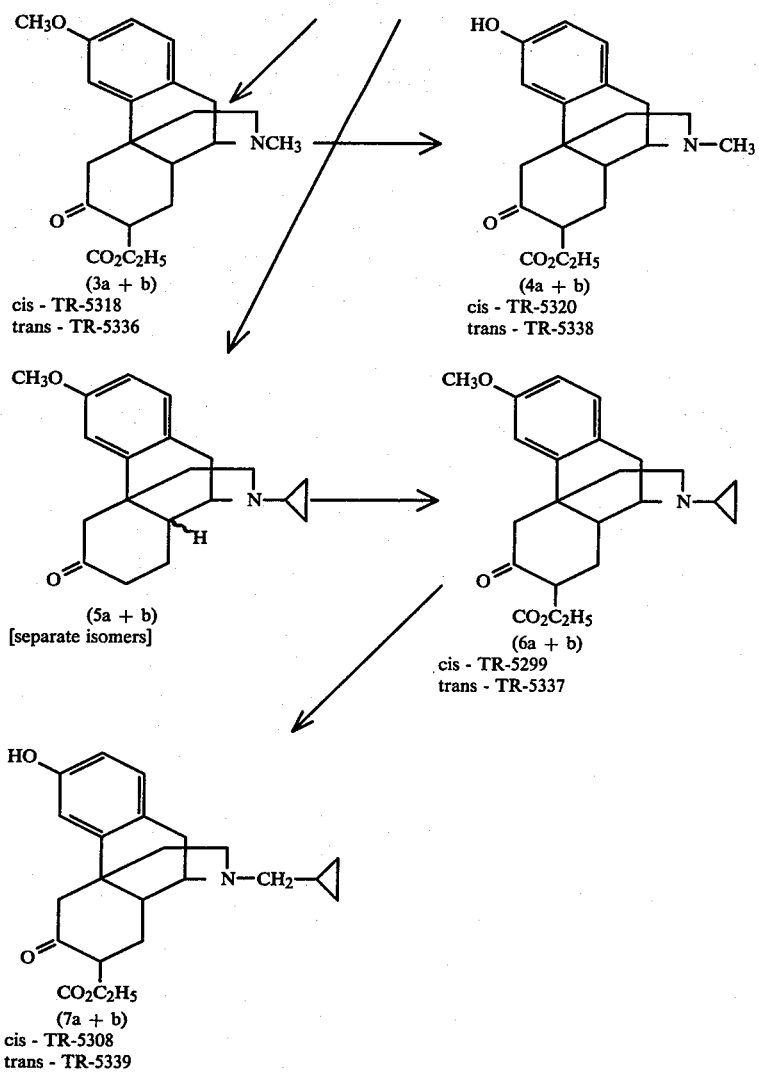

EXAMPLE I

A. General procedure for preparation of the 17-alkyl-7-carboethoxy-3-methoxy-morphinan-6-ones Sodium hydride (50% oil dispersion, 3.5 g, 84 mmol) was introduced into a reaction flask and, while kept under a $N_2$ atmosphere, was washed twice with hexane to remove mineral oil and then suspended in 100 ml of dry benzene. Diethylcarbonate (6.62 g, 56.1 mmol) was added and the mixture was heated to the reflux temperature. A solution of the appropriate 3-methoxy-17-alkyl-morphinan-6-one (14 mmol) in 60 ml of dry benzene was added dropwise to the hot slurry over a period of 2 hours, stirred an additional 3 hours at the reflux temperature and then left at ambient temperature overnight. The reaction was quenched by the addition of acetic acid followed by water and was then extracted with benzene (3 times), dried over $Na_2SO_4$ and concentrated in vacuo. The residue was taken up in $CH_2Cl_2$, washed twice with 5% $NaHCO_3$ and twice with water, dried over $Na_2SO_4$ and concentrated under reduced pressure. The crude product was purified by chromatography on Florisil using graded $MeOH/CHCl_3$ as eluant.

B.

7-carboethoxy-3-methoxy-17-methylmorphinan-6-one (TR-5318) was prepared in 38% yield from 3-methoxy-17-methylmorphinan-6-one) according to the general procedure outlined above.

NMR (CDCl$_3$) δ 1.2 (t, J=7 Hz, 3H), 2.42 (s, 3H, N—CH$_3$), 3.75 (s, 3H, O—CH$_3$), 4.1 (q, J=6 Hz, 2H), 6.65–7.12 (m, 3H, aromatics); IR (smear) 1650 cm$^{-1}$, 1720 cm$^{-1}$, 1740 cm$^{-1}$.

Anal. Calcd. for $C_{21}H_{27}NO_4.2/3$ $H_2O$; C, 68.27; H, 7.73; N, 3.79. Found: C, 68.49; H, 7.77; N, 3.79.

C.

7-carboethoxy-3-methoxy-17-methyl-14α-morphinan-6-one (TR-5336) was prepared in 86% yield from 3-methoxy-17-methyl-14α-morphinan-6-one according to the general procedure outlined above.

NMR (CDCl$_3$) δ1.32 (t, J=7 Hz, 3H), 2.37 (s, 3H), 3.77 (s, 3H), 4.23 (q, J=7 Hz, 2H), 6.63–7.1 (m, 3H, aromatics); IR (CHCl$_3$ solution) 1660 cm$^{-1}$, 1720 cm$^{-1}$, 1740 cm$^{-1}$.

Treatment with ethereal HCl provided the hydrochloride salt as a white solid: mp 154°–57° C.

Anal. Calcd. for $C_{21}H_{27}NO_4 \cdot HCl \cdot C_2H_5OH$: C, 62.93; H, 7.58; N, 3.19; Cl, 8.08. Found: C, 63.00; H, 7.10; N, 3.42; Cl, 8.09.

D.

7-carboethoxy-17-cyclopropylmethyl-3-methoxy-morphinan-6-one (TR-5299) was prepared in 31% yield from
17-cyclopropylmethyl-3-methoxy-morphinan-6-one according to the general procedure outlined above.

NMR $(CDCl_3)$ δ 0.07–0.53 (broad m, 4H, 17 H's), 1.23 (m, 3H), 3.72 (s, 3H), 4.07 (m, 2H), 6.57–7.03 (m, 3H); IR (smear) 1660 cm$^{-1}$, 1720 cm$^{-1}$, 1750 cm$^{-1}$.

Treatment with ethereal HCl provided the hydrochloride salt as a buff foam.

E.

7-carboethoxy-17-cyclopropylmethyl-3-methoxy-14α-morphinan-6-one (TR-5337) was prepared in 69% yield from
17-cyclopropylmethyl-3-methoxy-14α-morphinan-6-one according to the general procedure outlined above.

NMR $(CDCl_3)$ δ 0.08–0.52 (broad m, 4H, 17-H's), 1.32 (t, J=7 Hz, 3H), 3.77 (s, 3H), 4.25 (q, J=7 Hz, 2H), 6.62–7.08 (m, 3H); IR $(CHCl_3$ solution) 1660 cm$^{-1}$, 1710 cm$^{-1}$, 1730 cm$^{-1}$.

Treatment with ethereal HCl provided the hydrochloride salt as a tan foam.

F.

7-carboethoxy-17-cyclobutylmethyl-3-methoxy-morphinan-6-one (TR-5300) was prepared in 61% yield from 17-cyclobutylmethyl-3-methoxy-morphinan-6-one according to the general procedure outlined above.

NMR $(CDCl_3)$ δ 1.2 (t, J=7 Hz, 3H), 3.75 (s, 3H), 4.12 (q, J=7 Hz, 2H), 6.65 7.1 (m, 3H); IR (smear) 1660 cm$^{-1}$, 1720 cm$^{-1}$, 1750 cm$^{-1}$.

Treatment with ethereal HCl provided the hydrochloride salt as a buff foam.

Anal. Calcd. for $C_{25}H_{34}NO_4Cl \cdot 0.55$ $CHCl_3$. 0.75 $H_2O$: C, 62.86; H, 7.44; N, 2.87; Cl, 11.26. Found: C, 62.67; H, 7.14; N, 3.01; Cl, 11.52.

EXAMPLE II

General procedure for the preparation of the 17-alkyl-7-carboethoxy-3-hydroxy-morphinan-6-ones To a stirred solution of distilled $BBr_3$ (1.1 ml, 10.5 ml) in 10 ml of $CHCl_3$ was added dropwise a solution of the appropriate 17-alkyl-7-carboethoxy-3-methoxy-morphinan-6-one (0.87 mmol) (prepared in example I) in 10 ml of $CHCl_3$. After 0.45 hours, the reaction mixture was poured into an ice/$NH_4OH$ mixture and then stirred at 0° C. for 1 hour. The layers were separated and the aqueous phase was extracted twice with $CHCl_3$. The organic fractions were combined, washed once with water, dried over $Na_2SO_4$ and concentrated in vacuo. Purification of the product was effected by column chromatography over Florisil using graded MeOH/$CHCl_5$ as eluant.

A.

7-carboethoxy-3-hydroxy-17-methyl-14α-morphinan-6-one (TR-5338), m.p. 186°–188° C., was prepaed in 89% yield from
7-carboethoxy-3-methoxy-17-methyl-14α-morphinan-6-one according to the general procedure outlined above.

NMR $(CDCl_3)$ δ 1.27 (t, J=7 Hz, 3H), 2.37 (s, 3H), 4.18 (q, J=7 Hz, 2H), 5.9 (broad s, 1H, exchangeable), 6.55–7.03 (m, 3H); IR $(CHCl_3$ solution) 1660 cm$^{-1}$, 1720 cm$^{-1}$, 1740 cm$^{-1}$.

Anal. Calcd. for $C_{20}H_{25}NO_4 \cdot 0.5$ $H_2O$: C, 68.16, H, 7.44; N, 3.98. Found: C, 68.07; H, 7.50; N, 3.96.

B.

7-carboethoxy-3-hydroxy-17-methylmorphinan-6-one (TR-5320) was prepared as a tan foam in nearly quantitative yield from
7-carboethoxy-3-methoxy-17-methylmorphinan-6-one according to the general procedure outlined above.

NMR $(CDCl_3)$ δ 1.23 (broad m, 3H), 2.45 (s, 3H), 4.1 (broad m, 2H), 6.58–7.03 (m, 3H), 8.0 (broad s, 1H, exchangeable); IR $(CHCl_3$ solution) 1660 cm$^{-1}$, 1720 cm$^{-1}$, 1740 cm$^{-1}$.

C.

7-carboethoxy-17-cyclopropylmethyl-3-hydroxy-14α-morphinan-6-one (TR-5339) was prepared in 64% yield from
7-carboethoxy-17-cyclopropyl-methyl-3-methoxy-14α-morphinan-6-one according to the general procedure outlined above.

NMR $(CDCl_3)$ δ 0.03–0.5 (broad m, 4H), 1.32 (t, J=7 Hz, 3H), 4.27 (q, J=7 Hz, 2H), 5.1 (broad s, 1H, exchangeable), 6.6–7.07 (m, 3H); IR (smear) 1660 cm$^{-1}$, 1710 cm$^{-1}$, 1730 cm$^{-1}$.

Treatment with ethereal HCl gave the hydrochloride salt as a buff solid: mp—foams 205° C., melts 215°–220° C.

Anal. Calcd. for $C_{23}H_{30}NO_4Cl$, 0.5 $H_2O$, 0.05 $CHCl_3$: C, 63.66, H, 7.20; N, 3.22; Cl, 9.37. Found: C, 63.31; H, 7.15; N, 3.17; Cl, 9.51.

D.

7-carboethoxy-17-cyclobutylmethyl-3-hydroxy-morphinan-6-one (TR-5307) was prepared in 90% yield from
7-carboethoxy-17-cyclobutyl-methyl-3-methoxymorphinan-6-one according to the general procedure outlined above.

E.

7-carboethoxy-17-cyclopropylmethyl-3-hydroxy-morphinan-6-one (TR-5308) was prepared in 66% yield from
7-carboethoxy-17-cyclopropylmethyl-3-methoxymorphinan-6-one according to the general procedure outlined above.

NMR $(CDCl_3)$ δ 0.07–0.55 (broad m, 4H), 1.25 (m, 3H), 4.12 (m, 2H), 5.42 (broad s, 1H, exchangeable), 6.57–7.0 (m, 3H); IR (smear) 1660 cm$^{-1}$, 1720 cm$^{-1}$, 1740 cm$^{-1}$, 1750 cm$^{-1}$.

Treatment of TR-5308 with ethereal HCl afforded the hydrochloride salt as a buff foam.

PHARMACOLOGICAL EVALUATION

The compounds whose preparation is disclosed in the foregoing examples were screened to determine the following biological activities:

(A) Analgesic effects upon mice (acetic acid writhing test).
(B) Narcotic antagonist activity in rats (modified rat tail flick test).

TEST A

Acetic Acid Mouse Writhing Test

Analgesic effects of the test compounds were determined in mice by use of the acetic acid writhing test described by B. A. Whittle, *Brit. J. Pharmacol.*, 22:246 (1964). In this test, at least 3 groups of 5 male CD-1 mice each were given subcutaneous doses of the test drug dissolved in distilled water. In all cases, 0.4 milliliters of a 0.5% V/V acetic acid in distilled water solution was administered intraperitoneally 15 minutes post drug. The number of writhes in a 20 minute interval beginning 5 minutes after the acetic acid injection were determined and compared with the number of writhes in a control group which had received only acetic acid.

Percent inhibition of writhing was calculated as:

$$\% \text{ inhibition} = \left[ \frac{\text{No. Control Writhes} - \text{No. Treated Writhes}}{\text{No. Control Writhes}} \right]$$

The $ED_{50}$ dose, i.e., the dose required to reduce the number of writhes by 50%, was determined graphically from a plot of % inhibition as a probit verus log dose. Confidence limits of 95% were calculated on the basis of those results falling in the range 16–84% inhibition. See Lichtfield, J. T. and Wilcoxon, F., *J. Pharmacol. Exp. Ther.*, 96, 99–113 (1949).

TEST B

Evaluation of Narcotic Antagonist Activity

The narcotic antagonist effect of the test compound was determined by a modification of the rat tail flick procedure of Harris and Pierson (*J. Pharmacol. Exp. Ther.*, 143:141 [1964]).

Male albino Wistar rats (100–120 g) were used for this study. A rat's tail is so placed so as to cover a photocell. Heat is applied by a lamp in a reflector with a timer being connected to the lamp and photocell so that the timer goes on when the light is turned on and is turned off when the photocell is uncovered. A rheostat, incorporated into a heating lamp, is used to adjust the intensity of the light falling on the tail of the rat such that the rat's control reaction time is from 2 to 4 seconds. Animals with a control reaction time outside this range are rejected. The rheostat adjustment is made only if a significant proportion (1 out of every 10 rats) of the reaction times are outside the range of 2 to 4 seconds. Groups of 5 rats were used, and 2 control times were determined at 60 and 30 minutes prior to subcutaneous injection of the drug. A 10 second cutoff time is employed; if the rat does not flick the tail in 10 seconds it is removed from the heat source.

At least 30 minutes after the last control run the test drug was given intraperitoneally. This was followed 10 minutes later by an $ED_{80}$ dose of morphine subcutaneously. The animals were retested at 20 minutes after the morphine injection. Control animals were given vehicle and morphine only. The data were calculated as follows:

$$\% \text{ Effect } (E) = \left[ \frac{MRT^*(\text{Treated}) - MRT(\text{Control}) \times 100}{10 - MRT(\text{Control})} \right]$$

% Antagonism =

$$\left[ \frac{E(\text{morphine control}) - E(\text{Drug treated}) \times 100}{E(\text{morphine control})} \right]$$

*MRT is defined as mean reaction time.

The data were plotted on log-probit paper and $AD_{50}$ values, i.e., the dose required to inhibit the effect of morphine by 50% within 95% confidence limits, were determined by the method of Lichtfield and Wilcoxon.

The results obtained using the foregoing procedures are set out in Table I where IA means inactive at the dose indicated.

TABLE I

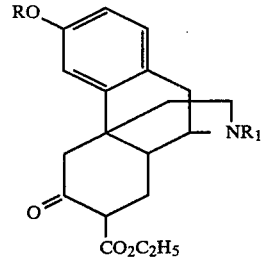

| Compound | Ex. | R | $R_1$ | B/C | $ED_{50}$ (mg/kg) | $AD_{50}$ (mg/kg) |
|---|---|---|---|---|---|---|
| TR-5318 | I B | $CH_3$ | $CH_3$ | cis | 4.6 | — |
| TR-5336 | I C | $CH_3$ | $CH_3$ | trans | >10.0 | — |
| TR-5299 | I D | $CH_3$ | CPM | cis | >10.0 | 13.0 |
| TR-5337 | I E | $CH_3$ | CPM | trans | IA 10.0 | >10.0 |
| TR-5320 | II B | H | $CH_3$ | cis | 0.72 | 3.6 |
| TR-5338 | II A | H | $CH_3$ | trans | 0.6 | 0.7 |
| TR-5308 | II E | H | CPM | cis | 4.9 | 3.12 |
| TR-5339 | II C | H | CPM | trans | 3.7 | 2.54 |
| TR-5300 | I F | $CH_3$ | CBM | cis | IA 10.0 | 13.0 |
| TR-5307 | II D | H | CBM | cis | 1.15 | >10.0 |

CPM = cyclopropylmethyl
CBM = cyclobutylmethyl

The compounds of the present invention form pharmacologically active addition salts with organic and inorganic acids. Typical acid addition salts are the tartrate, hydrobromide, hydrochloride and maleate. The hydrochloride is preferred. Typically, the free base of the compound will be dissolved in diluted hydrochloric acid (due to its low solubility in water) and the hydrochloride salt (which is water soluble) will be dissolved in distilled water so that the solutions prepared for administration of the compound will be chemically equivalent.

Those compounds which are pure analgesics are useful for relieving moderate to severe pain in an individual for whom such therapy is indicated whereas those compounds which have been found to be narcotic antagonists are useful for treating drug dependence in an individual for whom such therapy is indicated. Those compounds which are mixed analgesics/narcotic antagonists are useful for treating pain without the liability of drug dependence.

The term "individual" is intended to mean a human being or an experimental animal that is a model for a human being. The dose to be administered to achieve the desired result, i.e., the effective dose, may vary from individual to individual but is readily determined by one skilled in the art without undue experimentation.

The compounds of this invention may be administered by known, conventional methods of therapeutic administration such as intravenous, parenteral, buccal, rectal, or oral. Dose forms for the administration of these compounds can be prepared by methods recognized in the pharmaceutical sciences.

What is claimed is:

1. 7-carboethoxy-morphinan-6-one compounds characterized by the formula:

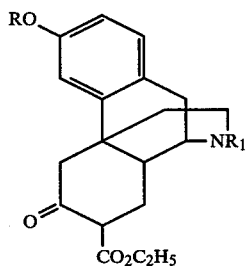

wherein R is H or methyl and $R_1$ is methyl, cyclopropylmethyl, cyclobutylmethyl, propargyl, allyl, dimethylallyl or furfuryl.

2. A compound as characterized by claim 1 wherein R is $CH_3$ and $R_1$ is $CH_3$ which compound is in the B/C cis configuration.

3. A compound as characterized by claim 1 wherein R is $CH_3$ and $R_1$ is $CH_3$ which compound is in the B/C trans configuration.

4. A compound as characterized by claim 1 wherein R is $CH_3$ and $R_1$ is cyclopropylmethyl which compound is in the B/C cis configuration.

5. A compound as characterized by claim 1 wherein R is $CH_3$ and $R_1$ is cyclopropylmethyl which compound is in the B/C trans configuration.

6. A compound as characterized by claim 1 wherein R is H and $R_1$ is $CH_3$ which compound is in the B/C cis configuration.

7. A compound as characterized by claim 1 wherein R is H and $R_1$ is $CH_3$ which compound is in the B/C trans configuration.

8. A compound as characterized by claim 1 wherein R is H and $R_1$ is cyclopropylmethyl which compound is in the B/C cis configuration.

9. A compound as characterized by claim 1 wherein R is H and $R_1$ is cyclopropylmethyl which compound is in the B/C trans configuration.

10. A compound as characterized by claim 1 wherein R is $CH_3$ and $R_1$ is cyclobutylmethyl which compound is in the B/C cis configuration.

11. A compound as characterized by claim 1 wherein R is H and $R_1$ is cyclobutylmethyl which compound is in the B/C cis configuration.

* * * * *

UNITED STATES PATENT AND TRADEMARK OFFICE
CERTIFICATE OF CORRECTION

PATENT NO.  : 4,423,221
DATED       : December 27, 1983
INVENTOR(S) : Raj Kumar Razdan and Haldean Cloyce Dalzell It is certified that error appears in the above-identified patent and that said Letters Patent are hereby corrected as shown below:

Cover page after "[73] Assignee" change "S/SA" to ---SISA---.

Column 3, line 34, change "rerystallized" to ---recrystallized---.

Column 5, beginning at line 13, insert ---Leland et al disclose the preparation of 7-methyl-3-methoxy- (or 3-hydroxy)-morphinan-6-ones and -isomorphinan-6-ones in J. Med. Chem., 23, 1427 (1980)---.

Column 5, line 25, extended line in formula should be directly over "N" instead of "$R_1$".

Column 7, compound (3a + b) the first "C" should be directly under the extended line at the 7 position instead of the second "C".

Column 7, compound (7a + b) the first "C" should be directly under the extended line at the 7 position instead of the second "C".

Column 8, compound (4a + b) the first "C" should be directly under the extended line at the 7 position instead of the second "C".

Column 8, compound (6a + b) the first "C" should be directly under the extended line at the 7 position instead of the second "C".

UNITED STATES PATENT AND TRADEMARK OFFICE
CERTIFICATE OF CORRECTION

PATENT NO. : 4,423,221
DATED : December 27, 1983
INVENTOR(S) : Raj Kumar Razdan and Haldean Cloyce Dalzell It is certified that error appears in the above-identified patent and that said Letters Patent are hereby corrected as shown below:

Column 10, line 3, change "prepaed" to ---prepared---.
Column 13, line 22, extended line in formula should be directly over "N" instead of "$R_1$".

*Signed and Sealed this*

*Thirtieth* Day of *October 1984*

[SEAL]

*Attest:*

GERALD J. MOSSINGHOFF

*Attesting Officer*     *Commissioner of Patents and Trademarks*